United States Patent [19]

DeBaun et al.

[11] Patent Number: 4,469,701
[45] Date of Patent: Sep. 4, 1984

[54] PYRROLID-3-EN-2-ONES AND PHARMACEUTICAL METHODS OF USE THEREOF

[75] Inventors: Jack R. DeBaun, Sunnyvale; Ferenc M. Pallos, Walnut Creek; Kent E. Matsumoto, Kensington; John H. Ross, San Jose, all of Calif.

[73] Assignee: Stauffer Chemical Company, Westport, Conn.

[21] Appl. No.: 507,246

[22] Filed: Jun. 23, 1983

[51] Int. Cl.³ .................. A61K 31/445; C07D 401/06
[52] U.S. Cl. .................................... 424/267; 546/276; 548/543
[58] Field of Search .......................... 546/208; 424/267

[56] References Cited
U.S. PATENT DOCUMENTS
4,110,105  8/1978  Teach .................................. 548/543
4,145,347  3/1979  L'Italien et al. .................... 546/208

Primary Examiner—Robert T. Bond
Attorney, Agent, or Firm—Elliott L. Fineman

[57] ABSTRACT

Novel compounds having the structural formula

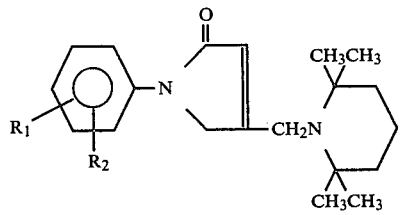

wherein $R_1$ and $R_2$ are independently selected from the group consisting of hydrogen, halo, alkyl, haloalkyl, thioalkyl, thiohaloalkyl, alkoxy, cyano and nitro are provided. The compounds have various pharmacological effects, including cardiotropic, hypoglycemic, hypocholesterolemic and/or antiulcerative effects in mammals. Methods of achieving these various pharmacological effects in mammals by administering the compounds thereto are provided. Pharmaceutical compositions and formulations including the compounds are provided along with methods of synthesis of the novel compounds.

44 Claims, No Drawings

PYRROLID-3-EN-2-ONES AND PHARMACEUTICAL METHODS OF USE THEREOF

BACKGROUND OF THE INVENTION

The invention concerns novel compounds and methods of use thereof to produce various cardiotropic effects in mammals. Other valuable pharmacologic effects in mammals may be obtained including regulation of serum glucose and serum steroid levels, especially cholesterol. Additionally, the compounds may be used to inhibit stress ulcers in mammals.

SUMMARY OF THE INVENTION

The inventors have discovered novel compounds having a number of pharmacologically valuable characteristics when used in mammals. The compounds have the following general formula:

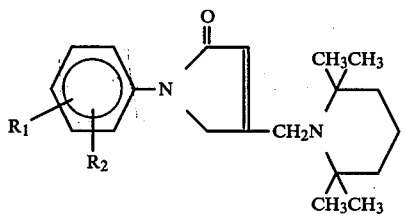

wherein $R_1$ and $R_2$ may be selected from the group consisting of hydrogen, halo, alkyl, haloalkyl, thioalkyl, thiohaloalkyl, alkoxy, cyano and nitro.

The term "lower alkyl" as used herein contemplates straight chain alkyl radicals containing from 1 to 6 carbon atoms and branched chain alkyl radicals containing 3 to 4 carbon atoms and includes methyl, ethyl, propyl, isopropyl, butyl, isobutyl, pentyl, hexyl and the like.

The term "lower alkoxy" as used herein contemplates both straight and branched alkoxy radicals containing from 1 to 4 carbon atoms and includes methoxy, ethoxy, isopropoxy, butoxy and the like.

The terms "halogen" and "halo" as used herein contemplate halogens and include fluorine,, chlorine, bromine and iodine.

Compounds of the general formula surprisingly possess a number of important pharmacological characteristics when applied in a number of forms to mammals. Compounds of the general formula have been found to possess significant cardiotropic, anti-ulcerative and other pharmacological effects.

Included in these effects are hypotensive activity, i.e., causing a reduction in blood pressure; bradycardiac activity, i.e., slowing of the heart beat; anti-arrythmic activity, i.e., reduction in cardiac arrhythmias and rapid heart beat in conditions which otherwise stimulate this activity; hypocholesterolemic activity, i.e., reduction in levels of serum cholesterol in mammals; hypoglycemic activity, i.e., decrease in glucose serum concentration; and anti-ulcer activity, i.e., reduction of stress related ulcers of the gastrointestinal tract.

In some cases multiple effects are manifest in a particular compound. In other cases one or another of these effects is found in a particular compound. Thus, compounds of the general class of compounds may be selected for a particular pharmacologic effect or for a complex of pharmacologic effects. Particular compounds of the general class are effective for hypotensive effects alone or anti-ulcerative effects alone, whereas other compounds of the general class are effective for combined hypotensive effects and other useful pharmacologic effects. Such combined effects include, for example, hypotensive and bradycardiac effects; hypotensive and anti-ulcerative effects; hypotensive, bradycardiac, hypocholesterolemic and anti-ulcerative effects; and hypotensive, bradycardiac, hypoglycemic, anti-ulcerative, but not hypocholesterolemic effects. Particularly unexpected is the apparent lack of central nervous system effects obtained by hypotensive effective doses of the same compounds of the general class. The method of achieving the above-described pharmacological effects in mammals in accordance with the invention comprises administering internally to a mammal a compound as represented by the general formula

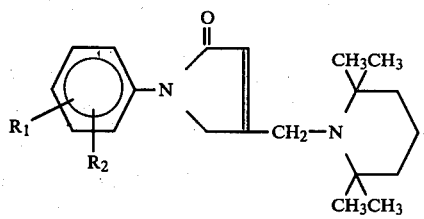

wherein $R_1$ and $R_2$ may be independently selected from the group consisting of hydrogen, halo selected from the group consisting of chlorine, bromine, fluorine and iodine, haloalkyl, thioalkyl, thiohaloalkyl, alkoxy, cyano and nitro in an amount effective for achieving a desired pharmacological effect.

In general, the synthesis of the compounds of the general class according to the invention are provided by alkylation of 2,2,6,6,-tetramethylpiperidine with the proper N-($R_1$-$R_2$-phenyl)-3-chloro-4-chloromethyl-2-pyrrolidinone wherein $R_1$ and $R_2$ may be independently selected from the group consisting of hydrogen, halo, alkyl, haloalkyl, thioalkyl, thiohaloalkyl, alkoxy, cyano and nitro.

In practice the compounds of the general class according to the invention may be synthesized by combining the properly substituted N-($R_1$-$R_2$-phenyl)-3-chloro-4-chloromethyl-2-pyrrolidinone with 2,2,6,6-tetramethylpiperidine in an organic solvent, for example, xylene, under an inert atmosphere for example $N_2$, and refluxing the components until the reaction is complete, followed by acid precipitation of the reaction product having the structural formula

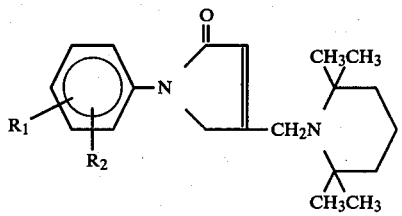

wherein $R_1$ and $R_2$ may be independently selected from the group consisting of hydrogen, halo, alkyl, haloalkyl, thioalkyl, thiohaloalkyl, alkoxy, nitro and cyano.

It is an object of the invention to provide new compounds having a range of valuable pharmacological effects in mammals and methods of use of compounds for achieving these pharmacological effects.

It is another object of the invention to provide compounds having hypotensive effects in mammals and furthermore to provide methods for the use of said compounds to achieve this hypotensive effect.

It is a further object of the invention to provide compounds having bradycardiac effects and methods of use of said compounds to achieve this bradycardiac effect.

It is yet another object of the invention to provide compounds having anti-arrythmic effects and methods of use of said compounds to achieve this anti-arrythmic effect.

It is still another object of the invention to provide compounds having hypo-cholesterolemic effects and methods of use of said compounds to achieve this hypo-cholesterolemic effect.

It is still a further object of the invention to provide compounds having hypoglycemic effects and methods of use of said compounds to achieve this hypoglycemic effect.

It is yet and still another object of the invention to provide compounds having anti-ulcerative effect and methods of use of said compounds for the production of this anti-ulcerative effect. These and other objects of the invention will be apparent to those skilled in the art from the following examples, which are intended by the inventors to be merely exemplary and not limiting to the scope of the invention.

EXAMPLE I

N-(3'-trifluoromethylthiophenyl)-3-chloro-4-chloromethyl-2-pyrrolidinone is prepared according to the method described in U.S. Pat. No. 4,110,105, which is herein incorporated by reference, and has the following structural formula:

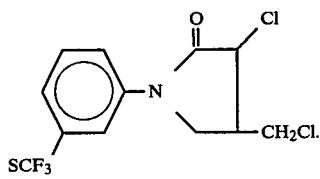

Eleven grams (g) (0.0315 mole) of this compound is combined with 13.7 g (0.0947 mole) of 2,2,6,6-tetramethylpiperidine and 20 milliliters (ml) of xylene in a 100 ml flask equipped with a thermometer, an $N_2$ bubbler, an air condenser and a magnetic stirrer. The mixture was refluxed until the reaction, as determined by gas chromatography, was complete. The mixture was then cooled and filtered and the filtrate was mixed with 20 ml of 4N HCl. A precipitate formed and was removed by filtration. The resulting filtrate was separated into organic and aqueous acid layers. The organic layer was washed twice with 20 ml of 4N HCl. The acid washes were combined, back-washed with 20 ml xylene, combined with the acid precipitate, mixed with 50 ml of dichloromethanechloride ($CH_2Cl_2$), cooled in an ice bath and basified with 25% sodium hydroxide (NaOH). An organic layer and an aqueous layer formed which were separated. The aqueous layer was washed twice with 25 ml of $CH_2Cl_2$. The $CH_2Cl_2$ washes were combined with the organic layer and dried over sodium sulfate ($Na_2SO_4$) and Florisil ®, a substance used for the removal of tar residues. The remaining liquid was filtered through a Florisil ® pad and the filtrate was stripped, yielding 1.7 g of a solid having a melting range of 145.0°–147.0° C. The compound, N-[3'-trifluoromethylthiophenyl]-4-[2'',2'',6'',6''tetramethylpiperidino]-methylpyrrolid-3-en-2-one has the following structural formula:

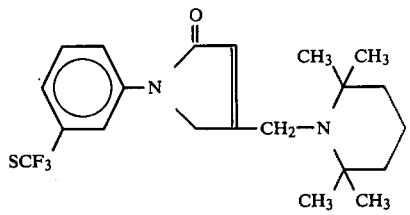

EXAMPLE II

The intermediate N-(3'-chlorophenyl)-3-chloro-4-chloromethyl-2-pyrrolidinone is prepared according to the method described in the abovementioned U.S. Pat. No. 4,110,105, and has the following structural formula

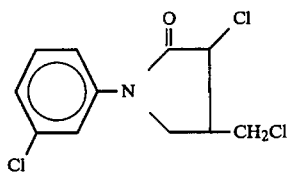

This compound is combined with 2,2,6,6-tetramethylpiperidine and xylene under the same conditions described in Example I hereinabove and is refluxed until completion of the reaction. The mixture is then cooled and filtered and the filtrate is acidified with 4N HCl. An acid precipitate forms and is removed by filtration. The organic layer of the filtrate is twice acid washed with 4N HCl. The acid washes are combined, back-washed with xylene, combined with the acid precipitate, mixed with an excess of $CH_2Cl_2$, cooled in an ice bath and basified with NaOH. The organic and aqueous layers which form are separated and the aqueous layer is twice washed with $CH_2Cl_2$. The $CH_2Cl_2$ washes are combined with the organic layer and dried over $Na_2SO_4$ and Florisil ®. The remaining liquid is filtered through a Florisil ® pad. The filtrate is stripped, yielding a solid having a melting point of between 130°–151° C. and the following structure:

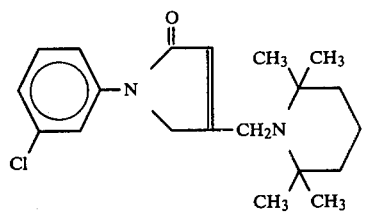

EXAMPLE III

The intermediate N-(3'-cyanophenyl)-3-chloro-4-chloromethyl-2-pyrrolidinone is prepared according to the method described in the above-mentioned U.S. Pat. No. 4,110,105 and has the following structural formula

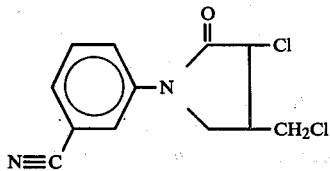

This compound is combined with 2,2,6,6-tetramethylpiperidine and xylene under the same conditions described in Example I hereinabove and is refluxed until completion of the reaction. The mixture is then cooled and filtered and the filtrate is acidified with 4N HCl. An acid precipitate forms and is removed by filtration. The organic layer of the filtrate is twice acid washed with 4N HCl. The acid washes are combined, back washed with xylene, combined with the acid precipitate, mixed with an excess of $CH_2Cl_2$, cooled in an ice bath and basified with NaOH. The organic and aqueous layers which form are separated and the aqueous layer is twice washed with $CH_2Cl_2$. The $CH_2Cl_2$ washes are combined with the organic layer and dried over $Na_2SO_4$ and Florisil ®. The remaining liquid is filtered through a Florisil ® pad. The filtrate is stripped, yielding a solid having a melting point of between 165°–170° C. and the following structure:

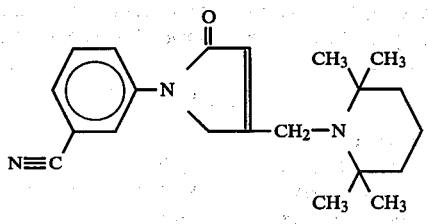

EXAMPLE IV

The intermediate N-[2'-chloro-5'-trifluoromethylphenyl]-3-chloro-4-chloromethyl-2-pyrrolidinone is prepared as follows: 50 g of 2-chloro-5-trifluoromethylaniline is combined with 34.8 g of triethylamine (TEA) and 200 ml of $CH_2Cl_2$. 48.6 g of dichloroacetyl chloride (DCAC) added dropwise while the mixture was kept at about 10° C. The mixture was stirred overnight forming a precipitate. The mixture was brought up to 1800 ml with $CH_2Cl_2$ and was washed 3 times (×) with 300 ml water, 3×300 ml 1.0N HCL and 3×300 ml saturated $NaHCO_3$. The precipitate was dried overnight with magnesium sulfate ($MgSO_4$) and stripped, yielding 59 g of 2'-chloro-5'-trifluoromethyldichloroacetanilide. 58.3 g of the 2'-chloro-5'-trifluoromethyldichloroacetanilide and 37.2 g of potassium carbonate ($K_2CO_3$) were combined with 300 ml acetone and heated with stirring to reflux in a 2 liter flask equipped with a thermal reflux condenser, drop funnel and $N_2$ bubbler. 39.1 g allyl bromide was added via the drop funnel at a constant temperature at 60° C. The mixture was refluxed for 2 hours and then stirred overnight. The mixture was filtered and stripped. 200 ml $CH_2Cl_2$ was added to the residue. This mixture was washed 3× with 100 ml $H_2O$ and 2× with 100 saturated NaCl solution. The filtrate was dried overnight in $MgSO_4$ and stripped to yield 55 g of N-allyl-2'-chloro-5'-trifluoromethyldichloroacetanilide.

45.0 grams of this product, 1.86 g of $Cu_2O$, 4.1 g of pyridine and 70 ml of toluene were placed in a reflux vessel and were refluxed for approximately 3 hours until the reaction was complete. The mixture was cooled and stripped and the remaining substance was taken up in $CH_2Cl_2$, washed 4× in 50 ml of 4N HCl. This product was filtered, dried over $MgSOI_4$, and stripped yielding 41.5 g of N-[2'-chloro-5'-trifluoromethylphenyl]-3-chloro-4-chloromethyl-2-pyrrolidinone.

Ten g of this compound was mixed with 16.3 g 2,2,6,6-tetramethylpiperidine and 30 ml of dimethylformamide, heated to reflux and refluxed for approximately 3 hours until the reaction was complete. The mixture was cooled, stripped, mixed with toluene and heated on a steam bath. The mixture was filtered hot and the precipitate was washed with hot toluene. The combined toluene washes were mixed with 50 ml 4N HCl, producing an acid precipitate which was removed by filtration. The filtrate was washed 2 times with 50 ml 4N HCl. The acid washes were combined and washed with 25 ml toluene, placed with the acid precipitate and 100 ml of $CH_2Cl_2$ in an ice bath and basified with 25% NaOH. Aqueous and organic layers formed which were separated and the aqueous layer was extracted 2 times with 50 ml $CH_2Cl_2$. The organic $CH_2Cl_2$ layers were combined, dried over $Na_2SO_4$ and Florisil ®, filtered through a Florisil ® pad stripped, yielding a solid which was mixed with hexane, filtered and dried, yielding 3.8 g of a product having a melting range of 140°–142° C., and a structural formula of

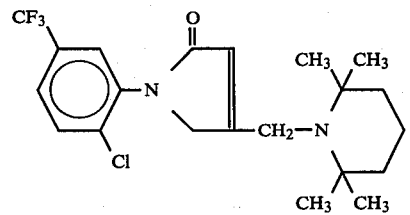

EXAMPLE V 45.0 g of 3,4-dimethoxyaniline, 32.6 g of TEA and 200 ml of $CH_2Cl_2$ were placed in a reflux vessel. 45.5 g DCAC and 200 ml $CH_2Cl_2$ were added over a one hour period at 10° C. and allowed to sit overnight. A precipitate formed. The mixture was brought up to 1800 ml with $CH_2Cl_2$ and was washed 3× with 300 ml $H_2O$, 3× with 300 ml 1.0N HCl and 3× with 300 ml of saturated $NaHCO_3$. The precipitate was stripped and dried overnight. 59.4 g of the dried precipitate was combined with 300 ml tetrahydrofuran (THF) and 5.2 g sodium hydride (NaH). The mixture was stirred until the NAH reaction subsided. The mixture was heated to reflux and 26.4 g of allyl bromide was added slowly. The mixture was refluxed for 4 hours. An additional 2.6 g NaH and 13.2 g allyl bromide were added and refluxed for 6 more hours. After the mixture cooled in an ice bath 2 ml $H_2O$ was added dropwise and the mixture was stripped. The mixture was brought up with 1 liter of $CH_2Cl_2$ was washed × with 300 ml $H_2O$, 3× with 300 ml 1.0N HCl and 3× with 300 ml saturated $NaHCO_3$. The organic layer was dried overnight with $MgSO_4$, filtered through Florasil ®, and was stripped to yield 50 g of product of 91% purity. The product was redissolved in 50 ml $CH_2Cl_2$ and put through a chromatographic column using 15 to 1 silica gel 60. 38 fractions were taken and assayed by thin layer chromatography. Fractions with the highest purities were recombined and stripped.

24 g of the resulting product was mixed with 1.0 g Cu$_2$O, 2.2 g pyridine and 50 ml of toluene and the mixture was refluxed for 6 hours until reaction was complete. The mixture was stripped, 500 ml CH$_2$Cl$_2$ was added and the resulting mixture was washed 4 times with 200 ml 4N HCl. The mixture was dried overnight with MgSO$_4$ and Florisil ®. The mixture was poured through an additional Florasil ® pad and stripped, yielding 19.4 g of product.

10.7 g of this product was combined with 19.9 g of 2,2,6,6-tetramethylpiperidine and 32 ml of dimethylformamide and was refluxed for 2 hours. The mixture was stripped and 200 ml toluene was added with stirring. The mixture was filtered and 200 ml of 4N HCl was added to the filtrate, which was then stirred. The acidified mixture was filtered and the precipitate was dissolved in 1 liter of CH$_2$Cl$_2$. 250 ml of H$_2$O were added and basified. The resulting aqueous layer was back-extracted 2 times with 50 ml CH$_2$Cl$_2$. The CH$_2$Cl$_2$ extracts were combined and washed 3 times with 250 ml H$_2$O. The mixture was then dried overnight with Na$_2$SO$_4$ and Florisil ® and run through a Florisil ® pad. The product was stripped yielding 5.8 g of a compound having a melting range of 185°–187° C. and a structural formula of

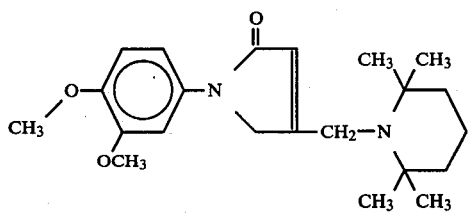

The following is a table of compounds that are prepared according to the above-mentioned procedures. Compound numbers are assigned to each and are used for identification throughout the remainder of the specification.

TABLE I

| Number | R$_1$ | R$_2$ |
|---|---|---|
| 1 | 3-CF$_3$ | H |
| 2 | 3-SCF$_3$ | H |
| 3 | 3-CF$_3$ | 5-CF$_3$ |
| 4 | 3-CH$_3$ | H |
| 5 | 4-F | H |
| 6 | H | H |
| 7 | 4-CF$_3$ | H |
| 8 | 4-SCH$_3$ | H |
| 9 | 2-Cl | H |
| 10 | 5-CF$_3$ | 2-Cl |
| 11 | 3-NO$_3$ | H |
| 12 | 3-OCH$_3$ | 4-OCH$_3$ |
| 13 | 3-Cl | H |
| 14 | 3-Br | H |
| 15 | 3-CN | H |

EXAMPLE VI

Evaluation of Compounds for Pharmacological Activity

A. Testing Procedures

Test solutions were prepared as aqueous solutions or finely homogenized suspensions (with addition of Tween 80) for administration. In some in vitro tests, small amounts of DMSO were utilized to increase solubility where this solvent does not interfere with the test. In vivo, results are usually expressed numerically as indicated for each test while results for in vitro tests may be expressed as + or − as described. In most cases, the "end results" best correlating with potential therapeutic effect is measured.

The following is a brief description of the testing procedure employed, expression of results and criteria employed. Activity of reference drugs should be of assistance in interpreting and comparing the data obtained on test compounds. The test is described briefly, the criterion is explained, and suitable reference compounds are listed followed by the ED-100 value in mg/kg or ug/ml representing the dose of the reference compound which is always active in the test system rather than the minimal effective dose (MED). The ED-100 is determined blind for test compounds in a given dose response experiment.

Following the description of all of the testing procedures employed, the results for each compound are set out by compound.

Test 1

Acute Toxicity:

Mice were dosed at 300 mg/kg, per oral (p.o.) and 200 ml/kg, interperitoneal (i.p.) for observation of any acute toxic symptoms or autonomic effects during the subsequent 72 hours. If none were noted, pharmacological evaluation proceeded employing doses and concentrations for each test based on appropriate multiples of doses required by suitable reference compounds. If acute toxicity was observed initially, the minimal toxic dose was determined and pharmacological screening doses were reduced proportionately.

Test 2

Antihypertensive:

Blood pressure was measured indirectly (tail cuff) in unanesthetized, unheated spontaneously hypertensive rats (SHR) before and 2, 4, and 6 hours after p.o. dosing. Reduction in mean pressure by more than 10% (>10) at any two consecutive measurement times after dosing indicates antihypertensive activity. The following are reference compounds and the ED-100 doses thereof.

| α-methyldopa | 50 | labetalol | 50 |
|---|---|---|---|
| hydralazine | 2.5 | nifedipine | 50 |
| guanethidine | 25 | phentolamine | 25 |
| prazosin | 1 | clonidine | <5 |
| mercamylamine | 10 | quanabenz | <6 |
| reserpine | 25 | captopril | 100 |

Test 3

Bradycardia:

To detect clonidine-like and bradycardic drugs, rats were dosed, p.o., followed 75 minutes later by determination of heart rate by EKG. Decrease in heart rate by more than 10% (>10) is considered a bradycardic effect. The following are reference compounds and the ED-100 doses thereof.

| clonidine | 0.5 | propranolol | 40 |
| --- | --- | --- | --- |
| quanabenz | 2.5 | reserpine | 5 |
| guanethidine | 20 | diltiazem | 10 |

Test 4

Antiarrhythmic:

Thirty minutes after i.p. dosing, if less than 2 (<2) of three mice tested displayed cardiac arrhythmia and heart rates above 200 beats/minute (EKG) when exposed to deep chloroform anesthesia, anti-arrhythmic activity is indicated. The following are reference compounds and the ED-100 doses thereof.

| qunidine | 100 | disopyramide | 50 |
| --- | --- | --- | --- |
| propranolol | 40 | verapamil | 50 |
| lidocaine | 50 | diltiazem | 50 |
| pindolol | 50 | nifedipine | 25 |
| mexilitine | 50 | procaine | 100 |

Test 5

Carbohydrate (CHO) Efficiency/Hypoglycemic:

Reduction of the glucose tolerance curve in starch loaded (2.5 g/kg) mice by more than 20% (>20) one hour after oral dosing indicates interference with carbohydrate digestion, glucose absorption or hypoglycemic activity. The following are reference compounds and the ED-100 doses thereof.

| tolbutamide | 50 | phenformin | 100 |
| --- | --- | --- | --- |
| glibenclamide | 1 | insulin subcutaneous (s.c.) | 0.25 U |

Test 6

Hypocholesterolemic:

Mice made hypercholesterolemic by being fed a high cholesterol-cholic acid diet for 7 days were dosed on the sixth and seventh days, p.o. After fasting overnight, reduction in serum cholesterol concentration by more than 15% (>15) from hypercholesterolemic control mice indicates activity. The following are reference compounds and the ED-100 doses thereof.

| clofibrate | 400 | diethylstilbestrol | 200 |
| --- | --- | --- | --- |
| bezafibrate | 200 | D-thyroxine | 10 |
| U-41792 | 200 | | |

Test 7

Hypoglycemic, mice:

Reduction in blood glucose concentration by more than 20% (>20) in fasted, glucose-loaded (1 gm/kg) mice one hour after dosing, p.o., indicates activity (test compound administered at same time as glucose load). The following are reference compounds and the ED-100 doses thereof.

| tolbutamide | 50 | glibenclamide | 1 |
| --- | --- | --- | --- |
| phenformin | 100 | insulin (s.c.) | 0.25 U |

Test 8

Antiulcer:

Fasted rats were dosed, p.o., 30 minutes before immobilization in wire mesh and partial immersion in water for 4 hours. Inhibition of the resulting stress induced gastric ulcers by more than 60% (>60) indicates activity. The following are reference compounds and the ED-100 doses thereof.

| atropine | 5 | pyridyl-2-thioacetamide | 50 |
| --- | --- | --- | --- |
| chlorpromazine | 20 | zolimidine | >100 |
| chlordiazepoxide | 100 | carbenoxolone | >100 |

Test 9

HP-betalipoprotein:

Reduction of serum heparin precipitating lipoprotein (HPL) concentrations (corresponding to low density lipoprotein and very low density lipoprotein fractions) in the same hypercholesterolemic mice from Test 6 above by more than 20% (>20) from control animals indicates activity. Reduction in the HPL/cholesterol ratio below 0.92 suggests increase in serum high density lipoproteins (HDL). The following are reference compounds and the ED-100 doses thereof.

| bezafibrate | 200 | D-thyroxine | 10 |
| --- | --- | --- | --- |
| U-41792 | 200 | diethylstilbestrol | 200 |

Test 10

Antiedema:

Rats are dosed p.o. one hour before intraplantar injection of carrigeenan (0.1 ml, 1% susp.). Inhibition of paw edema by more than 30% (>30) 3 hours after carriegeenan injection indicates acute anti-edema activity. The following are reference compounds and the ED-100 doses thereof.

| indomethacin | 4 | aspirin | 150 |
| --- | --- | --- | --- |
| diflunisal | 25 | phenylbutazone | 50 |
| ibuprofen | 25 | ketoprofen | 5 |
| hydrocortisone | 25 | naproxen | 5 |

Test 11

Pupil Dilation:

If the pupil diameter of mice exceeds 1.0 mm (>1) in bright light 30 minutes after dosing, i.p., ganglionic blockage or anti-cholinergic activity is indicated in the absence of adrenergic action. The following are reference compounds and the doses thereof.

| mecamylamine | 2.5 | atropine | 0.25 |
| --- | --- | --- | --- |

Test 12

Central Anticholinergic:

Inhibition of muscular tremors produced in mice by oxotremorine (0.5 mg/kg, s.c.) is scored one hour after i.p. injection of test compound. No tremor equals 0, mild tremor equals 1 and strong tremor equals 2. Maximum score—3 mice×2 equals 6. Scores less than 4 (<4)

indicate activity. The following are reference compounds and the ED-100 doses thereof.

| atropine | 2 | haloperidol | 10 |
|---|---|---|---|
| trihexyphenidyl | 10 | imipramine | 25 |
| clozapine | 10 | amitriptyline | 10 |
| thioridazine | 10 | tandamine | >50 |
| chlorpromazine | 2.5 | iprindole | >100 |
| metoclopramide | >100 | desipramine | >25 |
| sulpiride | >100 | tranylcypromine | >25 |

Test 13

Peripheral Antichloinergic:

Mice employed in Test 12 were observed for lacrimation (1 point) and salivation (1 point). Maximum score—3 mice×2 equals 6. Scores less than 4 (<4) indicate activity. The following are reference compounds and the ED-100 doses thereof.

| atropine | 0.25 | All other drugs listed in Test 12 were inactive at 25 mg/kg, i.p. |
|---|---|---|
| trihexyphenidyl | 2.5 | |
| clozapine | 10 | |
| amitriptyline | 25 | |

The results of the above-described tests are partially summarized in the following Table II.

TABLE II

| Compound Number | Effects | | | | | |
|---|---|---|---|---|---|---|
| | Antihypertensive[1] | A[2] | B[3] | C[4] | H[5] | U[6] |
| 1 | 19* | 0* | 14* | 5 | 14 | 75* |
| 2 | 14* | 3 | 6 | 0 | NA | 38 |
| 3 | 32* | 3 | 14* | 0 | NA | 38 |
| 4 | 23* | 2 | 19* | 25* | NA | 75* |
| 5 | 26* | 0* | 24* | 0 | NA | 75* |
| 6 | 18* | 3 | 20* | 12 | 29* | 75* |
| 7 | 16* | 3 | 12* | 0 | 22* | 38 |
| 8 | 25* | 3 | 18* | 0 | NA | 50 |
| 9 | 31* | 0* | 18* | 0 | 27* | 100* |
| 10 | 15* | 3 | 1 | 46* | NA | 75* |
| 11 | 27* | 3 | 5 | 0 | NA | 25 |
| 12 | 14* | 2 | 13* | 3 | NA | 75* |
| 13 | 4 | 3 | 1 | 13 | NA | 88* |
| 14 | 4 | 3 | 0 | 5 | NA | 50 |
| 15 | 19* | 3 | 0 | 15 | NA | 88* |
| Levels of Significance | >10 | <2 | >10 | >20 | >20 | >60 |

[1] Percent decrease in systolic blood pressure in spontaneously hypertensive rats 6 hr. after a 100 mg/kg oral dose.
[2] A = Antiarrythmic. Less than ⅜ mouse hearts fibrillating 15 min. after a 200 mg/kg intraperitoneal dose.
[3] B = Bradycardiac. Percent decrease in heart rate 45 min. after a 5 mg/kg oral dose in rats.
[4] C = Hypocholesterolemic. Percent decrease in serum cholesterol in hypercholesterolemic mice given 2 oral doses of 200 mg/kg drug candidate 20 hr. apart.
[5] H = Hypoglycemic. Percent decrease in serum glucose concentration in glucose loaded mice hr. following a 100 mg/kg oral dose.
[6] U = Anti-ulcerative. Percent inhibition of stress ulcers 4 hr. following a 50 mg/kg oral dose in rats.

Antihypertensive activity was confirmed in spontaneously hypertensive rats (SHR) at 100 mg/kg, p.o. in the apparent absence of autonomic effect or other pharmacological or toxic symptoms.

Compound No. 3:

Antihypertensive activity which appeared to be somewhat slow in onset but perhaps of long duration persisted at only 25 mg/kg, p.o. with a borderline result obtained at 10 mg/kg. Bradycardia was confirmed at 5 mg/kg, p.o. in rats with some evidence of motor impairment noted at 300 mg/kg. No evidence of autonomic inhibition was observed.

Compound No. 4:

Antihypertensive activity was generally comparable to that of Compound 3 with effects decreasing at 10 mg/kg. Bradycardia was again confirmed at 5 mg/kg, p.o. At 50 mg/kg, i.p., mouse pupils were significantly dilated suggesting possible clonidine-like release of adrenergic amines. Serum cholesterol and heparin precipitating lipoproteins (HPL) concentrations were reduced in hypercholesterolemic mice at 400 mg/kg, p.o. accompanied by a marked reduction in HPL/cholesterol ratio. Protection against stress-induced gastric ulcers was afforded rats at a hypotensive dose of 50 mg/kg, suggesting that lower doses may also be effective. Mice were protected from chloroform cardiac arrhythmias at doses of 200 mg/kg with borderline results at 100

Detailed Description of Test Results

Compound No. 1:

Hypotensive activity was confirmed at 50 mg/kg, p.o. in unanesthetized, normotensive rats with bradycardia confirmed at 10 mg/kg. Significant protection against stress-induced gastric ulcers was confirmed at 50 mg/kg, p.o. in the absence of notable central nervous system (CNS) depression or anticholinergic properties. Protection of mice from chloroform-induced cardiac arrhythmias was also observed at 50–100 mg/kg, i.p. This compound presents an unexpected profile of activity, especially in view of the apparent lack of acute toxicity.

Compound No. 2:

mg/kg of the compound i.p.

Compound No. 5:

Antihypertensive activity persisted at only 10 mg/kg, p.o. with borderline results obtained at 5 mg/kg in the absence of evidence of autonomic inhibition. Bradycardia was again confirmed at 5 mg/kg, p.o. Antiulcer and antiarrhythmic effects were noted at antihypertensive doses.

Compound No. 6:

Antihypertensive effects were confirmed at 25 mg/kg, p.o. with little evidence of autonomic effect, but was accompanied by bradycardia at only 2.5 mg/kg, p.o. Antiulcer and hypoglycemic effects were confirmed at doses of 100 mg/kg and 50 mg/kg, respectively.

Compound No. 7:
Profile generally similar to that of Compound 6.
Compound No. 8:
Profile generally similar to that of Compound 6.
Compound No. 9:
Antihypertensive activity persisted at 25 mg/kg, p.o. accompanied by bradycardia at 5 mg/kg. Pupillary dilation was again noted in mice at 25 mg/kg, i.p. which was not likely anticholinergic in nature but may reflect release of adrenergic amines shortly after injection in a manner similar to that seen with clonidine. The pupillary dilation does not appear to reflect ganglionic blockade because of the bradycardia noted. Antiedema effects occurred at doses exceeding 50 mg/kg, while antiulcer and antiarrhythmic effects occurred at hypotensive doses of 50 mg/kg and higher.

Compound No. 10:
Marked reductions in serum cholesterol and heparin precipitating lipoproteins (HPL) were accompanied by large reductions in HPL/cholesterol ratios at 200 and 400 mg/kg, p.o. suggesting increase in high density lipoprotein (HDL). No estrogenic effects or bradycardic effects were observed. Antihypertensive effects may be expected at doses exceeding 100 mg/kg. Rats were partially protected from stress-induced gastric ulcers at 50 mg/kg, p.o. in the absence of evidence of anticholinergic effects.

Compound No. 11:
Mild, rather slow onset antihypertensive activity was confirmed in SHR at 100 mg/kg, p.o. in the absence of bradycardia or autonomic inhibition.

Compound No. 12:
Profile generally similar to that of Compound 6.

Compound No. 13:
Protection against stress-induced gastric ulcers was confirmed at 25 mg/kg, p.o. in rats in the absence of CNS, anticholinergic or acute toxic effects.

Compound No. 14:
Antiulcer results were obtained, but activity appears to be weaker than with Compound 13.

Compound No. 15:
Antiulcer activity persisted at only 10 mg/kg, p.o. In the absence of CNS depression, anticholinergic or toxic effects, this represents unusual and strong activity. Hypotensive activity was also confirmed with this compound in unanesthetized, normotensive rats at 100 mg/kg, p.o.

It will be readily appreciated by those skilled in the art that the above-described compounds may be formulated with any one of a number of well known pharmaceutically acceptable carriers, depending upon the optimal route of administration, e.g., per oral or parenteral, including intravenous, intraperitoneal, intramuscular and subcutaneous.

Such carriers include solutions compatible with the mode of administration and solubility of the compounds. Such solutions may be buffered or otherwise formulated to minimize undesirable localized effects of injection if necessary. Formations for peroral administration are also well known to those skilled in this art and may be formulated for various effects, including timed, slow and delayed release. The compounds, formulated for these effects, may be administered in the form of tablets, linguents, capsules, suspensions, slurries and liquids. Such dosage forms may also include excipients, binders, fillers, flavorings, or sweetening agents or other therapeutically inert ingredients in the formulation of the desired pharmaceutical preparation.

Tablet forms may be coated or uncoated. Conventional excipients for tables include inert diluents such as magnesium carbonate or lactose, disintegrating agents such as maize starch or algenic acid.

Liquid carrier forms, for example, soft gelatin capsules, syrups, solutions and suspensions may be aqueous or oil-based, employing for example vegetable or animal oils such as sunflower oil, safflower oil, maize oil or cod liver oil.

For parenteral use, the compounds of this invention can be formulated with sterile ingredients compounded and packaged aseptically. They may be administered intravenously or intramuscularly. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is particularly useful. Up to 25-30% by volume of water may be incorporated in the vehicle if desired. An 80% aqueous propylene glycol solution is a particularly convenient solvent system. A pH range, about 7.4, and isotonicity compatible with body isotonicity, is desirable. Basicity may be controlled by the addition of a base as required, and a particularly convenient base is monoethanolamine. It may often be desirable to incorporate a local anesthetic and such are well known to those skilled in the art. The percentage of the compound to be used in the pharmaceutical carrier may be varied. It is necessary that the compound constitute a proportion such that a suitable dosage will be obtained.

The dosage required to achieve the desired pharmacologic activity in the mammal will vary with various factors such as route of administration, the species of mammal, general health and tolerances of the mammal, weight, sex and age of the mammal, the nature and severity of the disease being treated and the like. Additionally, it is to be noted that the exact dosage of each individual compound employed in similar situations will vary. Generally, a dosage would be in the range of from about 2.5 to about 400 milligrams or more per kilogram of body weight, and usually from 2.5 to about 100 milligrams per kilogram of body weight.

What is claimed is:
1. A compound of the formula

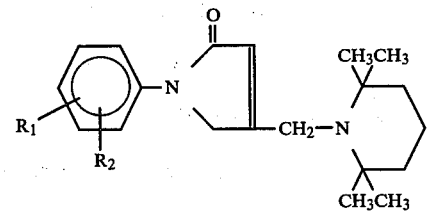

wherein $R_1$ and $R_2$ may be selected from the group consisting of hydrogen, halo, lower alkyl, halo lower alkyl, thiohalo-lower alkyl, thio-lower alkyl, lower alkoxy, cyano and nitro.

2. A compound of claim 1 wherein said halo is selected from the group consisting of chlorine, fluorine, bromine and iodine.

3. A compound of claim 2 wherein $R_1$ is halo and $R_2$ is hydrogen.

4. A compound of claim 3 wherein said halo is 2-chloro.

5. A compound of claim 3 wherein said halo is 3-chloro.

6. A compound of claim 3 wherein said halo is 3-bromo.

7. A compound of claim 3 wherein said halo is 4-fluoro.

8. A compound of claim 1 wherein said lower alkyl is methyl.

9. The compound of claim 8 wherein $R_1$ is 3-methyl, and $R_2$ is hydrogen.

10. A compound of claim 1 wherein said thio-lower alkyl is thiomethyl.

11. The compound of claim 10 wherein said $R_1$ is 4-thiomethyl and $R_2$ is hydrogen.

12. A compound of claim 1 wherein said thiohalo-lower alkyl is thiohalomethyl.

13. A compound of claim 12 wherein said thiohalomethyl is thiotrifluromethyl.

14. The compound of claim 13 wherein $R_1$ is 3-thiotrifluoromethyl and $R_2$ is hydrogen.

15. A compound of claim 1 wherein said halo-lower alkyl is halomethyl.

16. A compound of claim 15 wherein said halomethyl is trifluoromethyl.

17. A compound of claim 16 wherein $R_1$ is 4-trifluoromethyl and $R_2$ is hydrogen.

18. The compound of claim 16 wherein $R_1$ is 3-trifluoromethyl and $R_2$ is hydrogen.

19. A compound of claim 16 wherein $R_1$ and $R_2$ are trifluoromethyl.

20. The compound of claim 19 wherein $R_1$ is 3-trifluoromethyl and $R_2$ is 5-trifluoromethyl.

21. A compound of claim 1 wherein said lower alkoxy is methoxy.

22. A compound of claim 21 wherein $R_1$ and $R_2$ are methoxy.

23. The compound of claim 22 wherein $R_1$ is 3-methoxy and $R_2$ is 4-methoxy.

24. A compound of claim 1 wherein $R_2$ is halo selected from the group consisting of chlorine, bromine, fluorine and iodine.

25. A compound of claim 24 wherein $R_2$ is chloro.

26. A compound of claim 25 wherein $R_2$ is 2-chloro.

27. A compound of claim 1 wherein said halo lower alkyl is selected from the group consisting of chloro-lower alkyl, bromo-lower alkyl, fluoro-lower alkyl and iodo-lower alkyl.

28. A compound of claim 27 wherein said halo-lower alkyl is halomethyl.

29. A compound of claim 28 wherein $R_1$ is trifluoromethyl.

30. A compound of claim 29 wherein $R_1$ is 5-trifluoromethyl.

31. A compound of claim 1 wherein $R_1$ is cyano.

32. A compound of claim 31 wherein $R_1$ is 3-cyano.

33. A compound of claim 1 wherein $R_1$ is nitro.

34. A compound of claim 33 wherein $R_1$ is 3-nitro.

35. The compound of claim 1 wherein $R_1$ and $R_2$ are hydrogen.

36. A method of obtaining hypotensive, bradycardiac, antiarrythmic, anti-ulcerative, pupil-dilating, serum cholesterol reducing, serum glucose reducing or antiedema effects in a mammal comprising internally administering to said mammal an effective amount of a compound of the formula

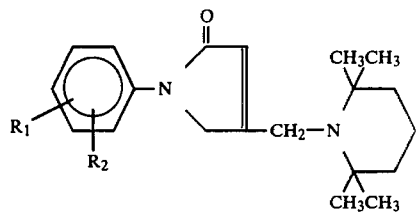

wherein $R_1$ and $R_2$ may be independently selected from the group consisting of hydrogen, halo, lower alkyl, halo lower alkyl, thiohalo-lower alkyl, thio-lower alkyl, lower alkoxy, cyano and nitro.

37. A method of claim 36 wherein said compound is administered in a dose range of from about 2.5 mg/kg weight of said mammal to about 1000 mg/kg weight of said animal.

38. A method of claim 37 wherein said compound is administered in a dose range of from about 2.5 mg/kg weight of said mammal to about 400 mg/kg weight of said animal.

39. A method of claim 36 wherein said compound is administered per orally.

40. A method of claim 36 wherein said compound is administered parenterally.

41. A method of claim 40 wherein said compound is administered intra-peritoneally.

42. A method of claim 36 wherein said compound is administered in a pharmacologically suitable carrier.

43. A process for making a compound of claim 1 comprising alkylating 2,2,6,6-tetramethylpiperidine with the compound having the formula

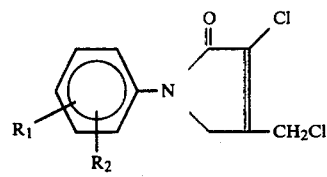

wherein $R_1$ and $R_2$ may be independently selected from the group consisting of hydrogen, halo, lower alkyl, halo lower alkyl, thiohalo-lower alkyl, thio-lower alkyl, lower alkoxy, cyano and nitro.

44. A process for making a compound of claim 1 comprising the steps of:
(a) combining 2,2,6,6-tetramethylpiperidine and a compound having the formula

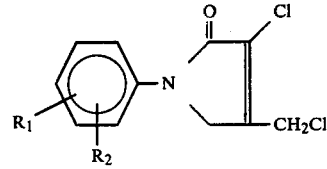

wherein $R_1$ and $R_2$ may be independently selected from the group consisting of hydrogen, halo, lower alkyl, halo lower alkyl, thiohalo-lower alkyl, thio-lower alkyl, lower alkoxy, cyano and nitro, in an organic solvent under an inert atmosphere;
(b) refluxing said combined 2,2,6,6-tetramethylpiperidine and said compound in said solvent until a reaction product is formed; and (c) isolating said reaction product having the structural formula
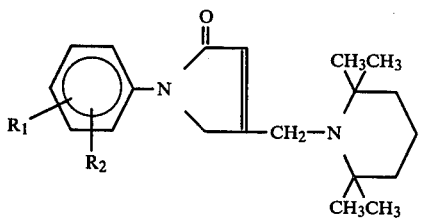
wherein $R_1$ and $R_2$ may be independently selected from the group consisting of hydrogen, halo, lower alkyl, halo lower alkyl, thio lower-alkyl, thio-halo lower alkyl, lower alkoxy, nitro and cyano.
* * * * *